United States Patent [19]

Kay

[11] 4,182,447

[45] Jan. 8, 1980

[54] DEVICE FOR STORING, TRANSPORTING AND MIXING REACTIVE INGREDIENTS

[76] Inventor: Ira Kay, P.O. Box 201, Haymarket, Va. 22069

[21] Appl. No.: 819,236

[22] Filed: Jul. 27, 1977

[51] Int. Cl.² ............................................. B65D 25/08
[52] U.S. Cl. ..................................... 206/220; 366/602
[58] Field of Search ................ 128/272; 206/219–220; 259/72, DIG. 20

[56] References Cited

U.S. PATENT DOCUMENTS

| 3,139,180 | 6/1964 | Kobernick | 206/220 |
| 3,275,302 | 9/1966 | Horton | 259/DIG. 20 |

FOREIGN PATENT DOCUMENTS

| 519008 | 4/1953 | Belgium | 206/220 |

*Primary Examiner*—Stephen Marcus
*Attorney, Agent, or Firm*—Sherman & Shalloway

[57] ABSTRACT

A device for storing, transporting and mixing reactive ingredients, such as mercury and silver for dental amalgam, includes a thin, rupturable membrane dividing the two chambers of a capsular container into two non-communicating closed compartments, one for each of the reactive ingredients, the chamber of larger volume (major chamber) also including a pestle. Unlike conventional devices of this type, the membrane is ruptured substantially completely intact, i.e. without presenting any loosened or torn fragments of the membrane which could contaminate the mixed ingredients simply by inserting the capsule in an amalgamator or similar vibrating or shaking device. Since no manipulation of the capsule, such as telescoping, bending, twisting etc is required, mixing of the components can be performed with a minimum amount of effort.

In an alternative embodiment, one of the substances to be mixed, such as silver powder for dental amalgam, is provided in the larger volume chamber in the form of a tablet or pellet and the pestle can be omitted. In this case, the tablet itself ruptures the membrane.

14 Claims, 8 Drawing Figures

DEVICE FOR STORING, TRANSPORTING AND MIXING REACTIVE INGREDIENTS

This invention relates to the art of disposable mixing devices and particularly, to relatively small compartmented capsular containers for storing, transporting and eventually triturating or intermixing carefully premeasured amounts of reactive ingredients separately contained in the compartments just prior to use of the triturated or intermixed ingredients.

There have been a large number of devices disclosed in the patent literature and commercialized for separately storing reactive ingredients, generally a solid substance and a liquid substance, which must be kept separated until just prior to use because of the relatively short shelf life of the mixed ingredients. Many of these prior art devices were particularly directed to the storage for subsequent mixing of premeasured quantities of dental preparations, such as silver powder and mercury for preparing dental amalgam. Generally, premeasured amounts of the individual ingredients are stored and shipped in separate compartments within the capsule and when ready for use are brought into contact with each other and triturated or intermixed.

Most usually, the ingredients are maintained in separate compartments or chambers by providing a membrane or other partition to divide the capsule into separate closed compartments. Just prior to use the membrane or partition is ruptured or otherwise displaced to provide communication between the previously separated closed compartments so that the ingredients may be mixed or triturated. Very often a pestle or other mixing aid is provided in one of the compartments to obtain more thorough mixing of the ingredients.

Mixing devices of this type are especially useful in the field of dentistry, and particularly for the preparation of dental amalgams from liquid mercury and silver wherein it is important to avoid contact with the mercury and to use carefully measured amounts of the reactive ingredients. The problem and extent of mercury contamination in dental offices has been described, for example, by Sidney L. Miller, et al., "Mercury Vapor Levels In The Dental Office: A Survey", JADA, Vol. 89, pages 1084–1098 (November 1974). The utilization of sealed mixing capsules containing premeasured quantities of mercury and silver, thereby avoiding any waste has therefore captured a substantial share of the commercial market for dental mercury.

However, all of these prior art devices suffer from the defect that in order to rupture or otherwise displace the separating membrane or partition, the capsules must either be telescoped, twisted, or otherwise manually manipulated by an operation requiring the full attention and both hands of the user. This is particularly disadvantageous, for example, for dentists and others, who must give their full attention to the patient or other area of work. For instance, in the case of a mixing capsule for epoxy or other adhesives, it would be advantageous to allow full attention to be given to the parts to be joined. It would, therefore, be highly desireable to provide a disposable mixing capsule of the type generally described above, which does not require any manual manipulation in order to rupture the separating membrane or partition to allow for trituration or intermixng of the premeasured ingredients.

Another problem inherent in the prior art devices of the type in which a separating membrane or partition must be ruptured to permit mixing of the previously separated ingredients is that any inadvertent pressure exerted during handling of the device can result in premature rupturing or displacement of the membrane. On the other hand, with some devices an excessive amount of pressure must be exerted on the capsule halves or body members to displace or rupture the separating membrane.

Still another problem with many prior art devices is that they require complicated and precision machining and additional components not present or required by conventional and commercially available capsules. Many of the prior art devices also suffer from the defect of being difficult to fill. These drawbacks are disadvantageous in view of the fact that these devices are usually intended to be disposable and the stringent requirements of the prior art devices can make the cost thereof relatively prohibitive.

The prior art patented devices can be broadly classified according to the following types: those in which telescoping (volume reduction) of the capsule halves or chambers causes the separating membrane to be displaced or ruptured: e.g. U.S. Pat. Nos. 1,774,258, 2,487,236, 2,527,992, 3,344,914, 3,451,540, 3,537,577, 3,595,439, 3,684,136, 3,796,303 and 3,809,225; those in which axial rotation of the capsule halves relative to each other (e.g. twisting), causes openings in separating partitions associated with each of the capsule halves to align with each other: e.g. U.S. Pat. Nos. 2,382,978 and 2,527,991; those in which a separate sealed pouch contained in one portion of the capsule and which must subsequently be ruptured contains the liquid component of the reactive ingredients: e.g. U.S. Pat. Nos. 3,415,360, 3,425,598, 3,638,918, 3,651,932 and 3,655,037; those in which it is necessary to partially unscrew the top member of the capsule to activate a valving mechanism: e.g. U.S. Pat. Nos. 3,139,180, 3,191,181 and 3,357,545; those in which a pullstring is attached to the separating partition for eventual displacement of the latter: e.g. U.S. Pat. Nos. 2,527,992 (also listed above) and 2,759,712.

All of the mixing capsules described in the above-mentioned patents and all of the presently commercially available devices known to applicant require some prior manipulation to activate the mixing capsule, i.e. displace or rupture the separating membrane so that the reactive ingredients can come into contact with each other.

It is accordingly an object of the present invention to provide an inexpensive mixing capsule in which premeasured amounts of reactive ingredients are maintained in separate closed compartments or chambers on either side of a separating membrane wherein the membrane can be ruptured simply by vigorously shaking the capsule.

It is a further object of the present invention to provide an inexpensive mixing capsule in which a pestle provided in one capsule chamber ruptures the separating membrane by vigorous shaking without any other manipulations.

It is still a further object of the present invention to provide such mixing capsule in which a pestle is omitted and rupturing of the separating membrane is accomplished by a tablet or pellet of a premeasured amount of a solid reactive ingredient.

It is still a further object of the present invention to provide a simplified process for mixing premeasured amounts of two reactive ingredients just prior to use does not require any manual dexterity and only a minimal amount of attention or concentration by the user.

A still further object of the present invention is to provide an inexpensive disposable mixing capsule from a commerically available or only slightly modified conventional capsule which can be filled and sealed in a simplified manner.

These and other objects of the present invention will become more apparent from the following description and accompanying drawings in which:

FIG. 1b is an exploded view of the capsule components of FIG. 1a;

Figure 1A:
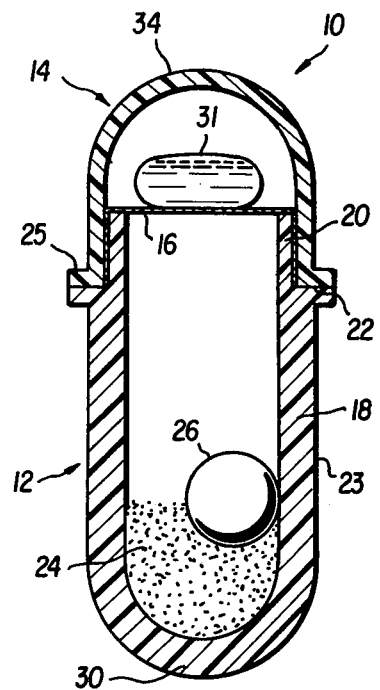
FIG. 1a is a vertical section view of one embodiment of the assembled capsular container of the present invention.

Briefly, these and other objects of the present invention are obtained by a device for storing, transporting and mixing premeasured amounts of reactive ingredients which must be kept separated until just prior to use, which is generally in the form of a sealed but openable capsular container formed from two opposed abutting substantially rigid, hollow chambers closed at opposite ends, a thin rupturable membrane dividing the container into separated closed compartments defined by the membrane and the hollow portion of each chamber, a premeasured amount of a first reactive ingredient and a freely movable pestle in one of the closed compartments and a premeasured amount of a second ingredient reactive with the first ingredient in the other closed compartment. The capsule can be opened by separating the chambers along the longitudinal axis of the capsule but, because the chambers abut against each other, the capsule cannot be telescoped (compressed) along the longitudinal axis to thereby exert pressure on the membrane by decreasing the volume (decreasing the length) contributed by the respective hollow chambers.

The chamber in which the pestle is placed should be long enough to allow the pestle to develop sufficient momentum to rupture the membrane when the capsular container is subjected to vigorous shaking, either manually or in a mechanical shaking device, such as an amalgamator.

It is also within the scope of this invention to omit the pestle by utilizing a a solid reactive ingredient in the form of a tablet or pellet. The tablet or pellet is sufficiently hard and firm to itself rupture the membrane but sufficiently reactive to completely intermix with the other, preferably liquid, reactive ingredient.

In a preferred embodiment the capsular container consists essentially of a first substantially rigid, hollow chamber member, including a substantially cylindrical body portion terminating at one end in a closed bottom portion and terminating at the opposed end in a cylindrical neck portion defining an opening into the first hollow chamber, the neck and body portions being integrally connected by a non-rupturable shoulder piece, and a second substantially rigid, hollow chamber member, including a substantially cylindrical body portion terminating at one end in a closed bottom portion and at the opposed open end in a radially outwardly extending flange. The two chambers are connected by a force fit of the open end of the second hollow chamber over the neck portion of the first hollow chamber with the flange substantially abutting the shoulder piece to thereby prevent any longitudinal movement (telescoping) of the first and second chamber members when the capsular container is in the closed operative condition. A thin, taut rupturable membrane is fixedly mounted over the opening in the neck portion of the first chamber to thereby define with the first hollow chamber a first closed compartment and with the second hollow chamber, a second closed compartment.

Since the first and second chambers are connected in fixed longitudinal relationship, i.e. the first and second chambers can not be telescoped one over the other to decrease the total volume of the capsular container, the rupturable membrane is protected against accidental rupturing or puncturing. Furthermore, even though the force fit may still allow relative rotation of the two chambers, such rotative movement will not cause rupturing or displacement of the membrane. Accordingly, only a deliberate vigorous shaking motion will cause the pestle or solid tablet or pellet of the reactive ingredient to develop sufficient momentum to rupture the separating membrane.

In accordance with the improved simplified method according to the present invention for mixing premeasured amounts of mutually reactive ingredients which must be separated until just prior to use and wherein the ingredients are stored in separated closed compartments above and below a separating partition or membrane in a generally capsular container wherein displacement or rupturing of the separating partition or membrane is required to permit mixing of the previously separated ingredients, a first reactive ingredient is stored in a first closed compartment defined by a first substantially rigid, hollow chamber formed from a generally cylindrical side wall, a closed end and an open end; and a second ingredient reactive with the first ingredient is stored in a second compartment defined by a second substantially rigid, hollow chamber formed from a generally cylindrical side wall, a closed end and an open end, the first and second hollow chambers together defining a closed capsular container when the members are connected in abutting open end to open end fixed longitudinal relationship. A thin, taut rupturable membrane is provided to separate the first and second reactive ingredients in their respective closed compartments. The membrane is fixedly mounted under tension over the open end of the first hollow chamber and also forms a barrier across the open end of the second hollow chamber. Freely movable rupturing means are provided within one of the first or second closed compartments to rupture membrane when the closed capsular container is subjected to vigorous shaking, such as mechanical agitation. The closed capsular container is then subjected to vigorous shaking to rupture the membrane and intermix the reactive ingredients. The rupturing of the partition and the mixing of the reactive ingredients is thereby accomplished solely by the vigorous shaking without requiring any manual or mechanical manipulation of the closed capsular container or the respective components thereof.

Reusable plastic capsular containers for preparing dental amalgams by the conventional technique of weighing out a predetermined amount of silver powder, placing the silver powder in one capsule half; placing one or more drops of mercury from a mercury dosimeter into the other capsule half, joining the capsule halves and placing the closed capsular container in an amalgamator, i.e. a high speed mechanical shaking device, for a prescribed time, are commercially available. It is possible to carry out the practice of the invention utilizing such commercially available reusable plastic capsules without any or only minor modifications to the capsule structure.

Generally, these capsules can be described as formed with substantially rigid walls as distinguished, for example, from conventional gelatin capsules used with medicinal preparations and which are thin and pliable. The capsules include two mating halves, i.e. hollow chambers, and generally one half will have a larger volume that the other, although that is not absolutely necessary since for some applications wherein relatively equal volumes of the reactive ingredients are employed, capsular containers having opposed mating havles of substantially equal or only slightly different volumes can be used. However, as will be described in more detail below, it is necessary that at least one chamber have sufficient volume, and especially sufficient length, to permit a pestle housed in that chamber to develop sufficient momentum to displace or rupture the separating membrane securely fixed over the open end of the chamber.

Also, unlike conventional gelatin capsules wherein each of the hollow chambers mating halves consist only of a cylindrical side wall and rounded closed bottom portions, the capsular containers which are useful in this invention include structure to positively prevent further telescoping or compressive longitudinal collapsing or sliding movement of the capsule halves. Most simply, this structure includes a reduced diameter cylindrical neck portion integrally connected to the main cylindrical walls, body portion of one of the hollow chambers, preferably the one of larger volume, through a shoulder piece extending substantially perpendicularly from the main body wall to the neck portion, and on the other hollow chamber a radially outwardly extending flange, such that when the latter is fitted over the neck portion of the former to close the capsule the flange will abut or rest against the shoulder piece.

By this arrangement, the separating membrane which is mounted under tension between the two hollow chambers to provide two separated closed compartments in the capsular container can not be accidently or prematurely ruptured or displaced by routine or normal handling during transportation or storage. Further, the fit of the smaller volume hollow chamber over the neck portion of the larger volume hollow chamber is made sufficiently tight so that it is not freely rotatable, i.e. a positive force must be applied to overcome the friction between the outside perpheral surface of the neck portion and inside peripheral surface of the other hollow chamber. Therefore, while the capsule halves may be rotated with respect to each other about the longitudinal axis of the capsule this rotation will not rupture or displace the separating membrane to inadvertantly or prematurely permit the reactive ingredients to intermingle with each other.

The tight fit is also necessary to prevent the reactive ingredients from spilling out of the assembled capsular container. It is understood that while the two chambers are in fixed abutting relationship when the filled capsular container is in operative condition, after the ingredients are thoroughly mixed the chambers are readily separable to provide access to the mixed or triturated ingredients. As used herein, the term "operative condition" or "activated condition" means that the capsule is ready to be placed in an amalgamator or other mechanical shaking or vibrating device or subjected to vigorous manual shaking to mix or triturate the reactive ingredients. It is a prominent advantage of this invention, and a distinguishing feature thereof that the capsule as stored and transported, i.e. when filled and closed in assembled condition, is in the operative condition and requires no telescoping or other exertion of pressure or manipulation.

While the disposable mixing capsules are particularly useful in storing, transporting and mixing dental preparations such as dental amalgams, restoratives and cements, they are also useful whenever it is necessary to keep mutually reactive substances separated until just prior to use, such as in the fields of cosmetics, medications, hair dyes, pigments, epoxy adhesives, cleansing solutions and the like. However, for the sake of simplicity, the invention will be described with particular reference to the preparation of dental amalgams from mercury and silver or silver alloy, powder or tablet.

In assembling the device, a premeasured quantity of silver powder and a pestle or silver pellet or tablet, alone or with a pestle are housed in the hollow chamber of larger volume and the access or opening into the chamber defined by the neck portion is covered with a thin, rupturable film of plastic or foil which serves as a rupturable separating membrane. The mercury in an amount corresponding to the amount of silver is placed in the other or small volume hollow chamber and the two chambers are then joined together in fixed abutting relationship to form the activated or operative capsular container. The closed capsule is immediately ready to be placed in any conventional amalgamator or mixing device for the appropriate amount of time, depending on the composition of the alloy and the speed of the amalgamator or mixing machine. This information is generally provided with the dental alloy. No manipulations, such as telescoping, pulling, turning, bending, etc. are required to rupture or displace the separating membrane since the pestle or silver tablet or pellet will be propelled in the agitator with sufficient velocity and momentum to rupture the membrane.

The separating membrane can be positively secured to the end and/or sides of the neck portion, as by heat welding or fusing when the membrane is formed from a thermoplastic material, for example. The membrane can also be adhesively secured to the end and/or sides of the neck portion. However, it is not necessary to positively secure the membrane to the neck portion.

It is sufficient that the membrane is of sufficient size to completely cover the opening in the neck portion and extend over the side walls thereof so that when the chambers are fully engaged in abutting relationship, i.e. the capsule is in assembled, closed condition, the film will be securely retained by the friction between the outside peripheral surface of the side walls of the neck portion and the inside peripheral surface of the cylindrical body wall of the other hollow chamber. It will therefore be understood that when the separating membrane is in position in the capsular container, two closed separated compartments will be formed from each of the hollow chambers with the membrane as a common dividing partition.

Generally, any rupturable plastic film or metallic foil can be used as the separating membrane. Elastomeric materials which can withstand high degrees of stretching or elongation without being ruptured or broken should be avoided. For example, plastic films, such as polyolefins, polyesters, polyvinyl chlorides, polyvinylidene chlorides and the like or aluminum or tin foils which are commercially available can be used. The film material should, of course, be inert to both of the reactive ingredients. The film is preferably about 1 mil thick, but can be slightly thicker or thinner so long as it can be ruptured by the pestle or pellet when the capsular container is subjected to vigorous shaking. The optimum film thickness and film tension are readily determinable by routine experimentation, but, in general, will depend on such factors as the type of pestle or pellet, the volume and length of the hollow chamber in which the pestle or pellet is located and the mechanical strength properties of the film. Clear plastic films are preferable to metal foils and especially preferred are plastic films formed from polyvinylidene chloride such as the type commercially available under the trademark, Saran Wrap, a product of the Dow Chemical Company. With Saran Wrap, experimentation has shown that when the film is sufficiently taut to present a wrinkle-free appearance, the membrane will be cleanly ruptured, that is, no loose or torn fragments are created to interfere with or contaminate the amalgam.

To provide more positive retention of the separating membrane between the capsule halves, the small volume hollow chamber is provided with an internal rim or seat located below the open end thereof at a distance substantially equal to the length of the neck portion of the larger volume hollow chamber, such that the end of the neck portion will abut against the internal rim.

In a further modification of the mixing capsule of the present invention, the progressive filling of the capsule is facilitated by providing a filler cap for an opening made in the closed end of the smaller volume hollow chamber. With this embodiment, in order to fill the capsule, the powdered or pelleted silver is introduced into the larger volume, hollow chamber through the opening in the neck portion and the pestle, which is optional when the powder is in the form of a tablet or pellet, is then inserted. The separating membrane is then stretched across the opening in the neck and the other hollow chamber, without the filler cap, is then seated over the neck with the flange seated against the shoulder piece. The mercury is then added through the opening in the closed end of the smaller chamber. Finally, the filler cap is seated in the opening to complete the assembly. It should be apparent that this embodiment of the present invention is readily adaptable to a continuous production or assembly line procedure.

The shape of the pestle is not particularly critical and can generally be of any shape, such as rod, sphere, oval, pyramidal and the like. Experiments have shown that a spherical pestle is particularly effective for providing complete trituration of the silver and mercury and a clean break or rupture of the separating membrane. The pestle can be formed from plastic or metal, but generally, plastic is preferred. As with the material of the separating membrane, the material of the pestle should be inert to the reactive ingredients and especially the reactive ingredient in the same closed compartment in which the pestle is housed.

Figure 1B:
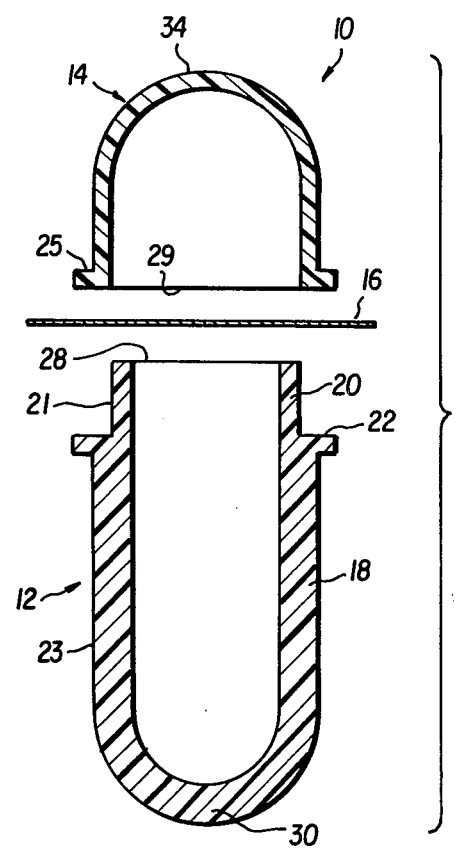

Looking at FIG. 1, the assembled capsular container, ready for use, is generally indicated at 10. The larger volume hollow chamber generally indicated at 12 is formed from substantially rigid, plastic material and has a major body portion 18, closed bottom portion 30 at one end and at the opposed end, a neck portion 20. A connecting or shoulder piece 22, which is substantially perpendicular to the cylindrical wall 21 of the neck portion and the cylindrical wall 23 of the main body portion joins the main body and neck portions.

The smaller volume, hollow chamber indicated generally at 14 includes a cylindrical body portion 15, a closed bottom portion 34 at one end and radially outwardly extending flange 25 at the opposed open end 29. The assembled capsular container for a dental amalgam preparation is about 1¼ inches in length of which about one-fourth to less than about one-half is attributed by the smaller capsule. A taut piece of thin, rupturable plastic film covers the opening of the neck portion to form separating membrane 16. The edges of the film are securely held between the outside periphery of the wall 21 and the inside periphery of the wall 15. The silver powder 24 and spherical plastic pestle 26 are housed in the closed compartment formed by the hollow chamber 12 and the membrane 16. The mercury 31 is separately housed in the closed compartment formed by the hollow chamber 14 and the membrane 16. The outwardly extending flange 25 at the open end of the chamber 14 abuts against the shoulder piece 22 of chamber 12. Accordingly, no further longitudinal displacement of the respective chambers is possible even if compressional forces are exerted on the ends or bottom portions 30 and 36. Further, rotational displacement of either chamber with respect to the other chamber, has no effect on the integrity of the seal provided by membrane 16. Therefore, the silver and mercury remain in their respective chambers indefinitely with no substantial risk of prematurely or inadvertently rupturing the separating membrane.

When the capsular container 10 is vigorously agitated, for example, in a conventional amalgamator such as normally found in a dentist's office, the motion causes the pestle to rupture the membrane and completely triturate the dental amalgam. Particularly when the membrane is formed from Saran Wrap or similar material, the membrane is perforated but is otherwise intact. This is a distinct advantage of the mixing device of the subject invention since it is not necessary to separate any part of the membrane material from the dental amalgam and no wastage of dental amalgam occurs.

Figure 2:
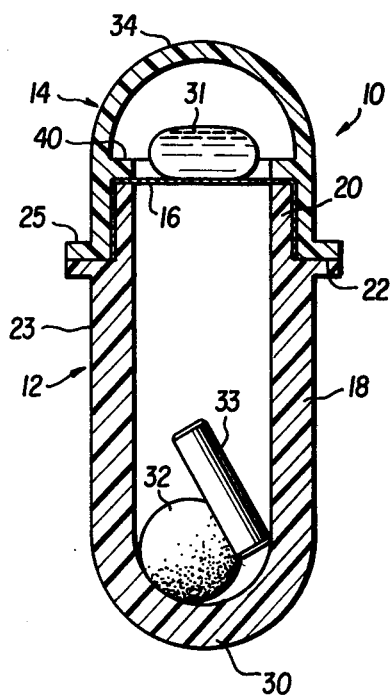
FIG. 2 is a vertical sectional view of a modified embodiment of the assembled capsular container of the present invention.

In the embodiment shown in FIG. 2, an internal seat or rim 40 is provided about halfway up the wall 18 of the smaller chamber 14. By making the length of the neck portion equal to the length of the side wall 15 between the rim 40 and the flange 25, the flange will abut against the shoulder piece 22 while the end 28 of the neck 20 will securely retain the membrane 16 against the rim 40. Silver pellet 32 (about 1/80 ounce) and cylindrical or rod-shaped pestle 33 are housed in the larger volume chamber 12 while liquid mercury (about 1/80 ounce or 1 drop) is housed in the smaller volume chamber 14, separated from the silver pellet by the separating membrane 16.

Figure 3:
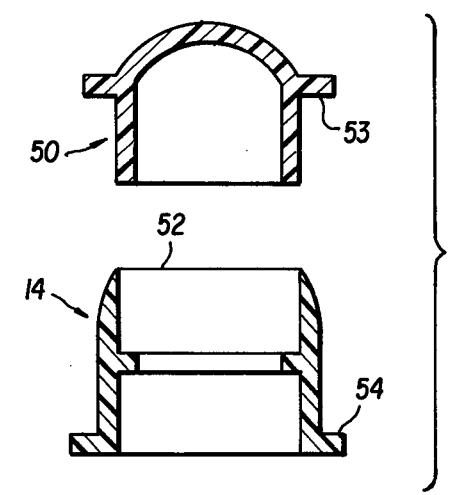
FIG. 3 is a vertical section view of a modified form of one portion of the capsular container.
Figure 4A:
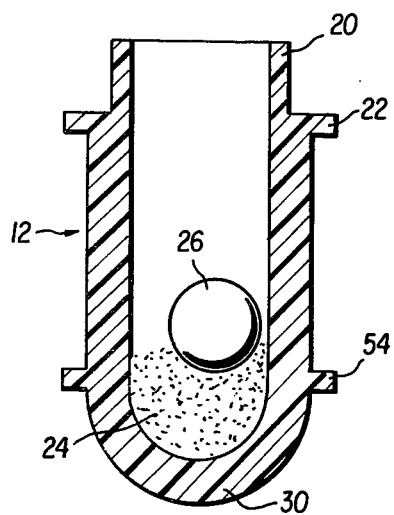
FIGS 4a-4b and 4c-4d illustrates the various sequential steps in filling the capsular container of a still further embodiment according to the present invention.
Figure 4B:
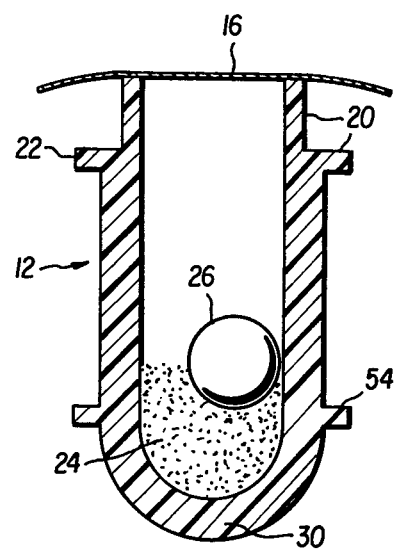
Figure 4C:
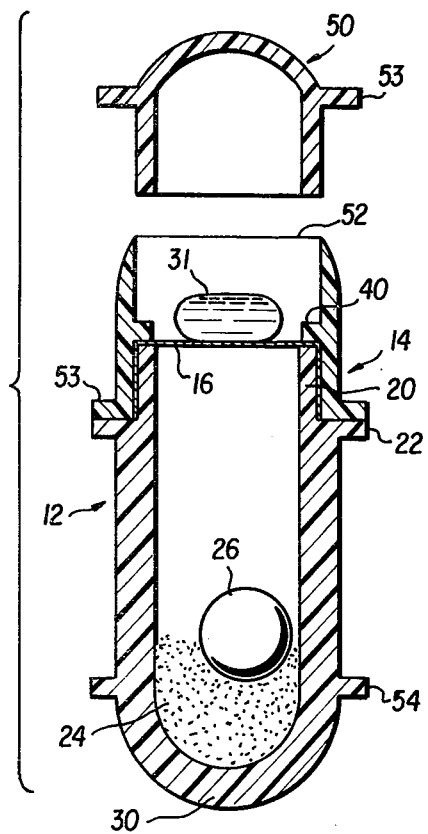
Figure 4D:
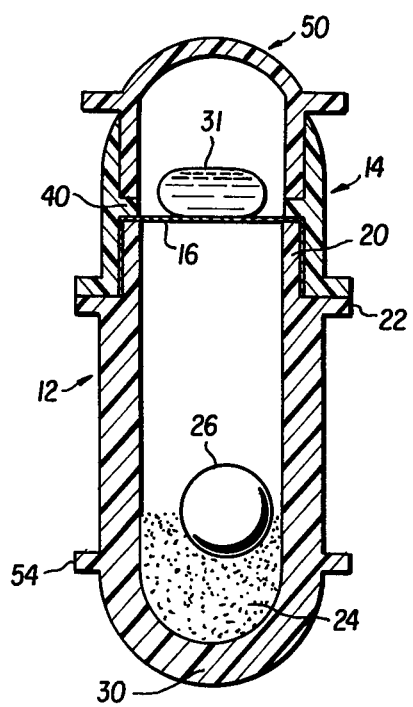

In the embodiment illustrated in FIG. 3, a perforation is made in the closed end of the upper capsule half and a filler cap 50 is provided to tightly close the opening 52. The opening 52 should be large enought to insert a drop of mercury. The filling operation of this embodiment is illustrated in FIG. 4. With the lower capsule half in a vertical upright position, the dental alloy and thereafter the pestle are inserted through the opening in the lower capsule half. The plastic film membrane is then tautly placed over the open end after which the upper capsule half, without the filler cap is seated over the neck of the lower capsule half. The mercury can then be filled through the opening 52 and the filler cap then placed in the opening to completely assemble the closed capsular container.

Also shown in FIG. 3 are additional external ridges 53 and 54 on each of the small and large hollow chambers. These ridges provide a better grip for the user. The hollow chambers can also be knurled to provide a good gripping surface.

The invention will now be described with reference to several examples which are of an illustrative, non-limiting nature.

EXAMPLE 1

A commercially available reusable plastic capsule of an acrylic resin material such as shown in FIG. 1 is opened and in the larger volume chamber (about 1½ inches long, including a ¼ inch long neck and about 5/16 inch internal diameter) there is inserted 1/80 ounce of silver powder and a commercially available spherical plastic pestle of about ¼ inch diameter. The mouth of this chamber is then sealed with a small piece of Saran Wrap. In the meantime, an equivalent weight (one drop) of mercury is placed in the smaller volume chamber (about ⅜ inch in length and about 13/32 inch internal diameter). With the piece of Saran Wrap held tautly over the mouth of the large chamber, the latter is inverted and the neck portion is fully inserted into the smaller chamber to close the capsule. The Saran Wrap therefore functions as a rupturable membrane separating the capsule into two closed compartments, one compartment containing silver powder and a pestle and the other containing mercury. The membrane will not be ruptured by routine handling and even when the closed capsule is dropped accidentally or forcefully, the membrane will not rupture. Rotating the smaller chamber over the neck portion of the larger chamber also will not rupture or displace the membrane. Only by subjecting the closed capsule to vigorous shaking to impart sufficient momentum to the pestle will the membrane be ruptured.

When the assembled capsular container is placed in a mechanical amalgamator completely triturated amalgam is obtained and the Saran Wrap separating membrane is observed to be perforated but otherwise intact.

Substantially identical results are obtained by using a commercially available steel rod pestle in place of the spherical plastic pestle.

EXAMPLE 2

Example 1 is repeated except that in place of the silver powder, a pellet of silver alloy of the same weight (1/80 ounce) is used and the pestle is omitted.

When the completed capsule is placed in an amalgamator, the membrane is ruptured and the ingredients are completely amalgamated. No fragments of the membrane are torn off to contaminate the amalgam and the amalgam is ready for use in a dental filling.

EXAMPLE 3

When Example 1 is repeated, but using a polyethylene film obtained from such commercially available sources as Glad-Wrap or Handiwrap plastic foils (of up to 3 mils in thickness), similar results are obtained but the membrane ruptures with more jagged edges and some small fragments may be torn off. However, it was found that these small fragments do not interfere with the amalgam and can be readily removed. Similar problems were encountered with aluminum foil used as the rupturable separating membrane.

It was also found that when the mercury is provided in a sealed metal foil pouch and the membrane is entirely omitted, the pouch will be ruptured when the capsule is placed in an amalgamator and the silver and mercury will be triturated. However, not all the mercury is freed from the pouch and some mercury will not be used in the amalgam. Therefore, the use of a sealed metal foil pouch to keep the mercury separated from the silver powder is not satisfactory.

While the invention has been described with reference to specific examples and embodiments, it will be apparent that other modifications and changes can be made without departing from the scope of the invention. For example, different sizes and shapes of the capsular container can also be used. It is also within the scope of the present invention to secure the capsule halves together in fixed abutting relationship by screwing the small volume chamber over the neck of the large volume chamber rather than by using a forced frictional fit. The use of a screw connection provides greater security against inadvertently opening the closed capsule but does require the use of two hands for unscrewing the capsule halves after mixing has been completed.

While various aspects of the invention have been set forth by the drawings and the specification it is to be understood that the foregoing detailed description is for illustration only and that various changes in parts, as well as the substitution of equivalent constituents for those shown and described, may be made without departing from the spirit and scope of the invention as set forth in the appended claims.

What is claimed is:

1. In device for storing, transporting and mixing premeasured amounts of two mutually reactive ingredients which includes
    a sealed capsular container formed from two opposed, abutting substantially rigid, hollow chambers closed at opposite ends and opened at the joined abutting ends,
    a thin, rupturable membrane fixedly mounted over the open end of one of said hollow chambers and dividing the container into separated closed compartments, defined by the membrane and the hollow portion of each chamber, respectively,
    a premeasured amount of a first reactive ingredient housed in one of said closed compartments,
    a premeasured amount of a second reactive ingredient housed in the other of said closed compartments, and
    a freely movable rupturing means housed in one or the other of said closed compartments and capable of rupturing said membrane when the device is subject to vigorous shaking,
    wherein the container can be opened by separating the respective chambers along the longitudinal axis of the container but the respective chambers cannot be telescoped one over the other to thereby exert pressure on said membrane; the improvement comprising using polyvinylidene chloride as said rupturable membrane, whereby upon subjecting said device to vigorous shaking the membrane will rupture to permit intimate mixing and reaction of said first and second reactive ingredients without any portion of said ruptured membrane from interfering with or contaminating the reacted ingredients.

2. The device according to claim 1 wherein said first substantially rigid hollow chamber includes a cylindrical major body portion terminating at one end in a closed bottom portion and at the other end in a cylindrical neck portion defining an opening into said first chamber, and a non-rupturable shoulder piece connecting the cylindrical neck portion to the cylindrical body portion, and second substantially rigid hollow chamber including a cylindrical body portion terminating at one end in a closed bottom portion and at the other open end in a radially outwardly extending flange, the open end of the second chamber frictionally engaging the neck portion of the first chamber and the flange of the second chamber abutting against the shoulder piece of the first chamber; whereby said chambers are connected in fixed longitudinal relationship to define a closed capsular container.

3. The device according to claim 2 wherein the membrane is tautly mounted over the open end of said first hollow chamber and fixedly retained in position between the outside peripheral surface of said neck portion and the inside peripheral surface of said second chamber.

4. The device according to claim 2 wherein said second hollow chamber further includes an internal rim located below the open end thereof a distance substantially equal to the length of said neck portion of the first hollow chamber, whereby the end of the neck portion will abut against said internal rim.

5. The device according to claim 1 wherein the reactive ingredients together form a dental preparation selected from the group consisting of dental restoratives and dental cement.

6. The device according to claim 1 wherein the rupturable membrane is a polyvinylidene chloride film of about 1 mil thickness.

7. The device according to claim 1 wherein said rupturing means is a pestle.

8. The device according to claim 1 wherein said rupturing means is said first reactive ingredient in the form of a solid pellet or tablet.

9. The device according to claim 1 wherein one of said hollow chambers is provided with a sealable opening in the closed end thereof, and a removal cap sealing said opening.

10. The device according to claim 1 wherein said hollow chambers are of unequal volume and said rupturing means is housed in the chamber of larger volume.

11. The device according to claim 1 wherein said first and second reactive ingredients are silver and mercury in premeasured quantites to form a dental amalgam.

12. In a method for mixing premeasured amounts of mutually reactive ingredients which must be separated until just prior to use wherein the ingredients are stored in separate closed compartments on either side of a separating partition or membrane in an assembled, closed, capsular container, wherein displacement or rupturing of the separating partition or membrane is required to permit mixing of the previously separated ingredients, said mixing being effected by the steps of:

storing a first reactive ingredient in a first closed compartment of a capsular container, said first compartment defined by a first substantially rigid, hollow chamber comprising a generally cylindrical side wall, a closed end and an open end and a thin, taut rupturable membrane fixedly mounted over said open end;

storing a second ingredient reactive with the first ingredient in a second closed compartment in said capsular container, said second closed compartment defined by a second substantially rigid, hollow chamber comprising a generally cylindrical side wall, a closed end and an open end; said first and second hollow chambers being removably connected in abutting open end to open end fixed longitudinal relationship to form said assembled capsular container;

providing rupturing means freely movable within one of said first or second closed compartments to rupture said membrane when the closed capsular container is subjected to vigourous shaking, and subjecting the closed capsular container to vigorous shaking to rupture the rupturable membrane and intermix the reactive ingredients; whereby the rupturing of the partition and mixing of the reactive substances is accomplished solely by said rupturing means as a result of vigorous shaking without requiring any manual or mechanical manipulation of the closed capsular container or the respective components thereof; the improvement comprising using polyvinylidene chloride as said rupturable membrane, whereby upon subjecting said device to vigorous shaking the membrane will rupture to permit intimate mixing and reaction of said first and second reactive ingredients without any portion of said ruptured membrane from interfering, with or contaminating the reacted ingredients.

13. The method according to claim 12 wherein said rupturing means is a pestle.

14. The method according to claim 13 wherein said reactive ingredients are silver and mercury in premeasured quantities to form a dental amalgam.

* * * * *